(12) United States Patent
Tripathi et al.

(10) Patent No.: US 11,612,614 B2
(45) Date of Patent: Mar. 28, 2023

(54) ISOMORPHS OF REMDESIVIR AND METHODS FOR SYNTHESIS OF SAME

(71) Applicant: Anzalp Pharmasolutions Pvt. Ltd., Indore (IN)

(72) Inventors: Vinay Shankar Tripathi, Indore (IN); Akshay Nikhil Patel, Indore (IN)

(73) Assignee: ANZALP PHARMASOLUTIONS PVT. LTD., Indore (IN)

( * ) Notice: Subject to any disclaimer, the term of this patent is extended or adjusted under 35 U.S.C. 154(b) by 51 days.

(21) Appl. No.: 17/145,274

(22) Filed: Jan. 8, 2021

(65) Prior Publication Data

US 2021/0161927 A1    Jun. 3, 2021

(30) Foreign Application Priority Data

Oct. 20, 2020    (IN) .............................. 202021045737

(51) Int. Cl.
*A61K 31/706*    (2006.01)
*A61K 9/00*    (2006.01)

(52) U.S. Cl.
CPC .......... *A61K 31/706* (2013.01); *A61K 9/0019* (2013.01)

(58) Field of Classification Search
None
See application file for complete search history.

(56) References Cited

U.S. PATENT DOCUMENTS 10,251,904 B2 *    4/2019    Clarke ............... A61K 31/4184

OTHER PUBLICATIONS

US, Arya Lekshmii, Sowparnika Treasa Sabu, and Shaiju S. Dharan. "A Scrutiny On Role of Remdesivir in COVID-19 Pandemic." (2020).*

* cited by examiner

*Primary Examiner* — Patrick T Lewis
(74) *Attorney, Agent, or Firm* — Dickinson Wright PLLC (57) ABSTRACT

A new isoform of 2-ethylbutyl (2S)-2-[[[(2R,3S,4R,5R)-5-(4-aminopyrrolo[2,1-f][1,2,4]triazin-7-yl)-5-cyano-3/4-dihydroxyoxolan-2-yl]methoxy-phenoxyphosphoryl]amino] propanoate (Remdesivir) having increased water solubility is disclosed, along with methods for making the same. Also disclosed are solid and liquid pharmaceutical compositions suitable for treating viral infections such as Arenaviridae, Coronaviridae, Filoviridae, Flaviviridae, or Paramyxoviridae viral infections which contain an effective amount of Remdesivir prepared according to the inventive method and the use of those compositions for treating such viral infections.

4 Claims, 3 Drawing Sheets

REMDESIVIR

FIGURE 1C

ISOMORPHS OF REMDESIVIR AND METHODS FOR SYNTHESIS OF SAME

FIELD OF INVENTION

The present invention relates to a new isomorph of 2-ethylbutyl (2S)-2-[[[(2R,3S,4R,5R)-5-(4-aminopyrrolo[2,1-f][1,2,4]triazin-7-yl)-5-cyano-3,4-dihydroxyoxolan-2-yl]methoxy-phenoxyphosphoryl]amino]propanoate, which is more commonly known as Remdesivir, and methods of making the same. The present invention also relates to solid and liquid pharmaceutical compositions suitable for treating viral infections such as Arenaviridae, Coronaviridae, Filoviridae, Flaviviridae, or Paramyxoviridae viral infections which contain an effective amount of the new isomorph of Remdesivir and the use of those compositions for treating such viral infections.

BACKGROUND OF THE INVENTION

The treatment of viral infections caused by Arenaviridae, Coronaviridae, Filoviridae, Flaviviridae, and/or Paramyxoviridae presents challenges due to a lack of vaccine or post-exposure treatment modality for preventing or managing infections caused by viruses from these families. In some cases, patients only receive supportive therapy such as electrolyte and fluid balancing, oxygen, blood pressure maintenance, or treatment for secondary infections. This problem has become particularly apparent during the current COVID-19 pandemic caused by the Coronoavirus SARS-CoV-2.

Remdesivir is a broad-spectrum antiviral prodrug of an adenosine triphosphate (ATP) analog, with potential antiviral activity against a variety of RNA viruses. Remdesivir, being a prodrug, is metabolized into its active form GS-441524 upon administration. As an ATP analog, GS-441524 competes with ATP for incorporation into RNA and inhibits the action of viral RNA dependent RNA polymerase. This results in the termination of RNA transcription and decreases viral RNA production in the body.

Remdesivir is known to exhibit antiviral properties against Arenaviridae, Coronaviridae, Filoviridae, and Paramyxoviridae viruses as described, for example, in Warren, et al., Nature 531:381-385 (2016), U.S. Pat. Nos. 9,724,360, 9,949,994, 10,065,958, and 10,695,361. Remdesivir is also known to exhibit antiviral properties against Flaviviridae viruses as described in International Publication No. WO 2017/184668, U.S. Pat. Nos. 8,008,264, 8,318,682, and RE46762. Moreover, Remdesivir has recently been approved by the U.S. Food & Drug Administration for the treatment of patients with COVID-19 and is currently the only small molecule available for such use.

Remdesivir has the following structural formula:

Remdesivir is a white to off-white or yellow non hygroscopic solid, practically insoluble in water and soluble in ethanol. Remdesivir has six chiral centres and is produced as a single stereoisomer. The molecular formula is $C_{27}H_{35}N_6O_8P$ and the molecular weight is 602.6 g/mol.

For a number of reasons, Remdesivir must be administered parenterally to patients in need thereof. Remdesivir, however, is relatively insoluble in water and chemically unstable in aqueous media. Different polymorphic forms of Remdesivir exist and the active substance in the current commercial product is manufactured as Form II or mixtures of Form II and another crystalline form. The mixture of forms and Form II show similar solubility and do not result in differences in finished product performance.

Consequently, in the past, it has been proposed to combine Remdesivir with one or more solubilizers in order to improve its solubility for administration parenterally. See, e.g., U.S. Pat. No. 10,675,296. Such solubilizers, however, may have certain undesirable effects described in Stella, et. al. Toxicologic Pathology, 36(1):30-42 (2008). For example, a formulation including polysorbate 80 may have potential hemodynamic effects, tubing limitations, extractables and leachables from tubing, limitations on stoppers, potential for precipitation upon dilution, or issues with adaptability for pediatric use. Similarly, beta-cyclodextrin derivatives are known to have certain physiological effects on kidneys, thus there is also a need to limit the amount of such solubilizers in a pharmaceutical formulation.

There therefore remains a need for compositions comprising Remdesivir, or pharmaceutically acceptable salt thereof, that exhibits improved solubility, improved usability for parenteral administration, and sufficient room-temperature and elevated temperature stability to avoid the use of cold-chain for transport and/or storage.

As shown in Scheme 1 below, U.S. Pat. No. 9,724,360 discloses a method for preparing phosphoramidate prodrug (6) by oxidizing a commercially available tribenzyl protected lactol 1 to its corresponding ribolactone 2 by treating with acetic anhydride in DMSO. The C—C bond forming glycosylation reaction of the ribolactone 2 with a bromo pyrrolotriazine nucleus 3, facilitated by N-silyl protection of 3, followed by a lithium-halogen exchange using excess BuLi at −78° C. The lithiated pyrrolotriazine was coupled with ribolactone 2 to provide a mixture of V isomers of nucleoside 4 followed by 1'-cyanation to give the β-anomer 5 after chromatographic purification. Tribenzyl deprotection of β-anomer 5 gave the 1-cyano modified adenine nucleoside 6.

Scheme 1

1

-continued

A diastereomeric mixture of the phosphoramidoyl chloridate prodrug moiety 8 was prepared from the L-alanine analogue 7, as shown in Scheme 2 below:

Scheme 2

8
diastereoisomeric mixture

Finally, coupling of nucleoside 6 and chloridate 8 provided the phosphoramidate prodrug mixture 9 in ~1:1 diastereomeric ratio. The two diastereomers can be resolved using chiral HPLC to afford the Sp isomer 9a and Rp isomer 9b, as shown in Scheme 3 below:

Scheme 3

9
1:1 diastereoisomeric mixture chiral HPLC

9a
Sp isomer
Remdesivir and

9b
RP isomer

Tiago Vieira, et al. have developed a batch synthesis process for the cyanation of a remdesivir precursor that can be operated at −30° C., as described in "Large-Scale Cyanation Process Using Continuous Flow Chemistry en Route to the Synthesis of Remdesivir," *Organic Process Research & Development*, 24(10): 2113-2121 (2020). As shown below, the cyanation

1

2

-continued remdesivir reaction was performed with trifluoroacetic acid (TFA) instead of TfOH and added a precooled mixture of TMSOTf and TMSCN in dichloromethane (DCM) to obtain good diastereo-selectivity at −30° C.

Improvement of the C-glycosylation step in the synthesis of Remdesivir to obtain ribofuranoside adduct with higher yields by utilizing diisopropylamine is reported in *Organic Process Research & Development*, 24: 1772-1777 (2020).

Despite these efforts, there remains a need in the art for an improved synthesis for preparation of Remdesivir, with good yields and high purity. There also remains a need for new isoforms of Remdesivir, particularly those exhibiting improved pharmacological properties such as increased solubility in water and greater availability.

SUMMARY OF THE INVENTION

It is therefore an object of the present invention to provide a more aqueous-soluble form of Remdesivir for parenteral administration to patients in need thereof.

In accordance with these and other objects, a first embodiment of the present invention is a method for the synthesis of Remdesivir, which comprises:

(a) reacting (3R,4R,5R)-3,4-bis(benzyloxy)-5-((benzyloxy)methyl)dihydrofuran-2(3H)-one with iodopyrazole in presence of boron trichloride in an organic solvent at room temperature to form (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol;

(b) cyanating the (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol formed in (a) to produce (3R,4R,5R)-2-(4-aminopyrrolo[2,1-f][1,2,4]triazin-7-yl)-3,4-bis(benzyloxy)-5-((benzyloxy) methyl)tetrahydrofuran-2-carbonitrile;

(c) hydrolyzing the (3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile produced in (b) in presence of boron trichloride to give (3R,4S,5R)-2-(4-aminopyrrolo[2,1-f][1,2,4]triazin-7-yl)-3,4-dihydroxy-5-(hydroxymethyl)tetrahydrofuran-2-carbonitrile; and (d) condensing the (3R,4S,5R)-2-(4-aminopyrrolo[2,1-f][1,2,4]triazin-7-yl)-3,4-dihydroxy-5-(hydroxymethyl)tetrahydrofuran-2-carbonitrile formed in (c) with 2-ethylbutyl (chloro(phenoxy)phosphoryl)-L-alaninate to produce Remdesivir.

According to other embodiments of the present invention, reaction (d) above is replaced by:

(d1) reacting (3R,4S,5R)-2-(4-aminopyrrolo[2,1-f][1,2,4]triazin-7-yl)-3,4-dihydroxy-5-(hydroxymethyl)tetrahydrofuran-2-carbonitrile formed in (c) with 2,2 dimethoxy propane in the presence of PTSA and isopropylacetate to form (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile; and (d2) reacting the (3aR,4R,6R,6aR)-4-(4-aminopyrrolo[2,1-f][1,2,4]triazin-7-yl)-6-(hydroxymethyl)-2,2-dimethyltetrahydrofuro[5 3,4-d][1,3]dioxole-4-carbonitrile formed in (d1) with t-BuMgCl in presence of 2-ethylbutyl (chloro(phenoxy)phosphoryl)-L-alaninate to produce Remdesivir.

Another embodiment of the present invention is a form of Remdesivir having improved aqueous solubility that has been prepared according to the methods disclosed herein.

Other embodiments of the present invention are pharmaceutical compositions for parenteral administration, including lyophilized compositions for reconstitution prior to use, comprising an effective amount of a form of Remdesivir having improved aqueous solubility and prepared according to the methods disclosed herein.

Still other embodiments of the present invention are methods treating a viral infection, such as COVID-19, in a mammal, such as a human, by administering an effective amount of a form of Remdesivir having improved aqueous solubility and prepared according to the methods disclosed herein

DETAILED DESCRIPTION OF PREFERRED EMBODIMENTS

I. General

Figure 1A:
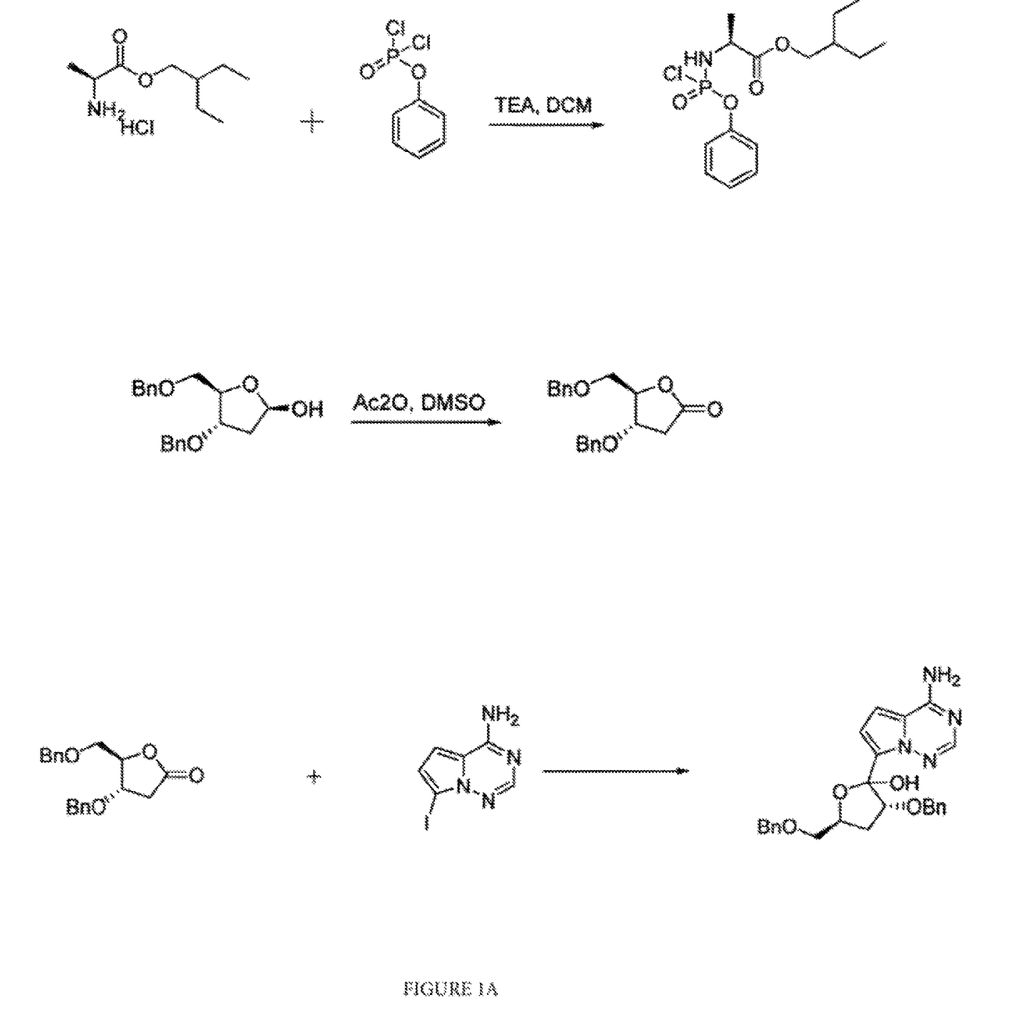
FIGS. 1A-1C depict the route of synthesis of Remdesivir according to the present invention.
Figure 1B:
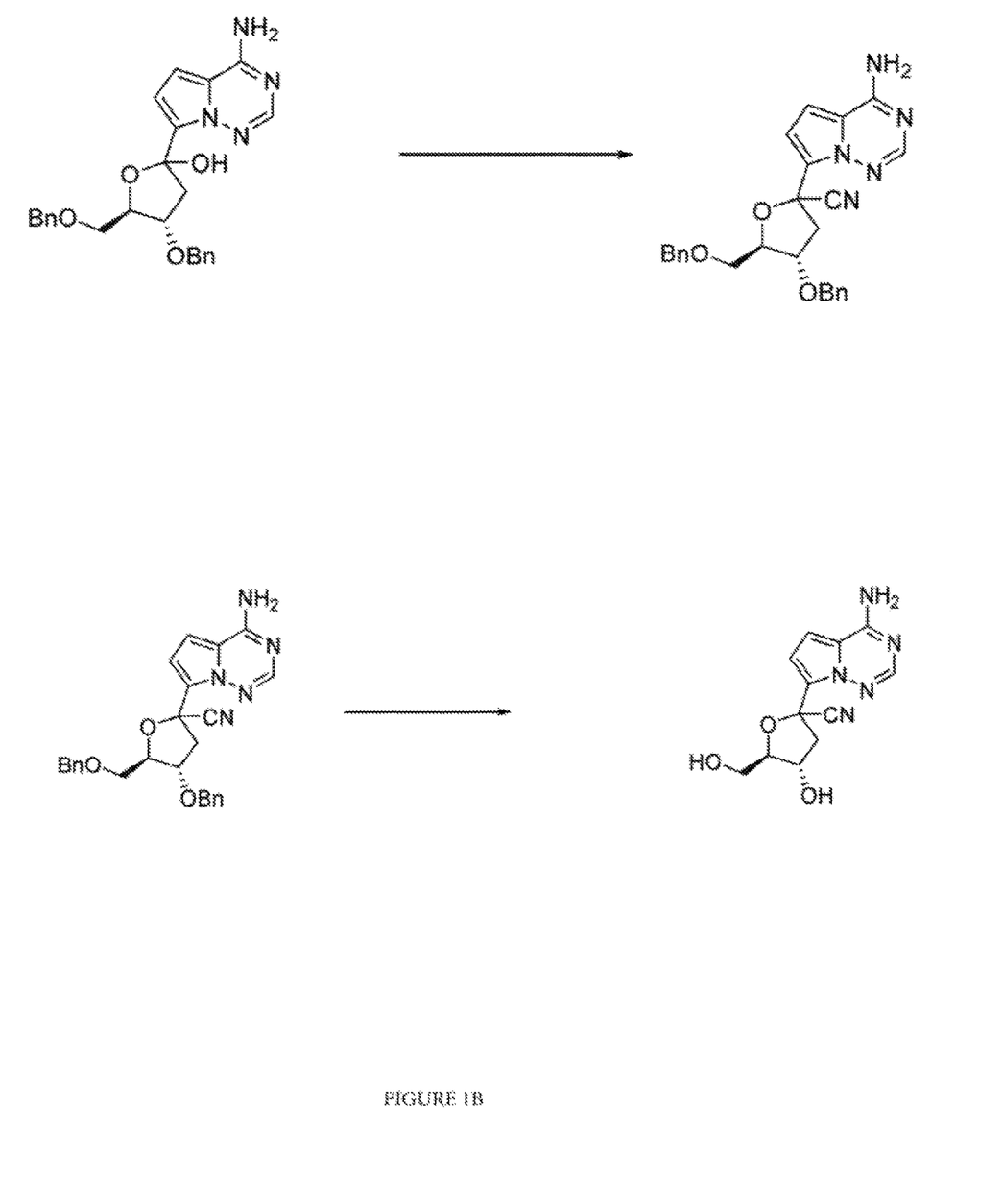
Figure 1C:
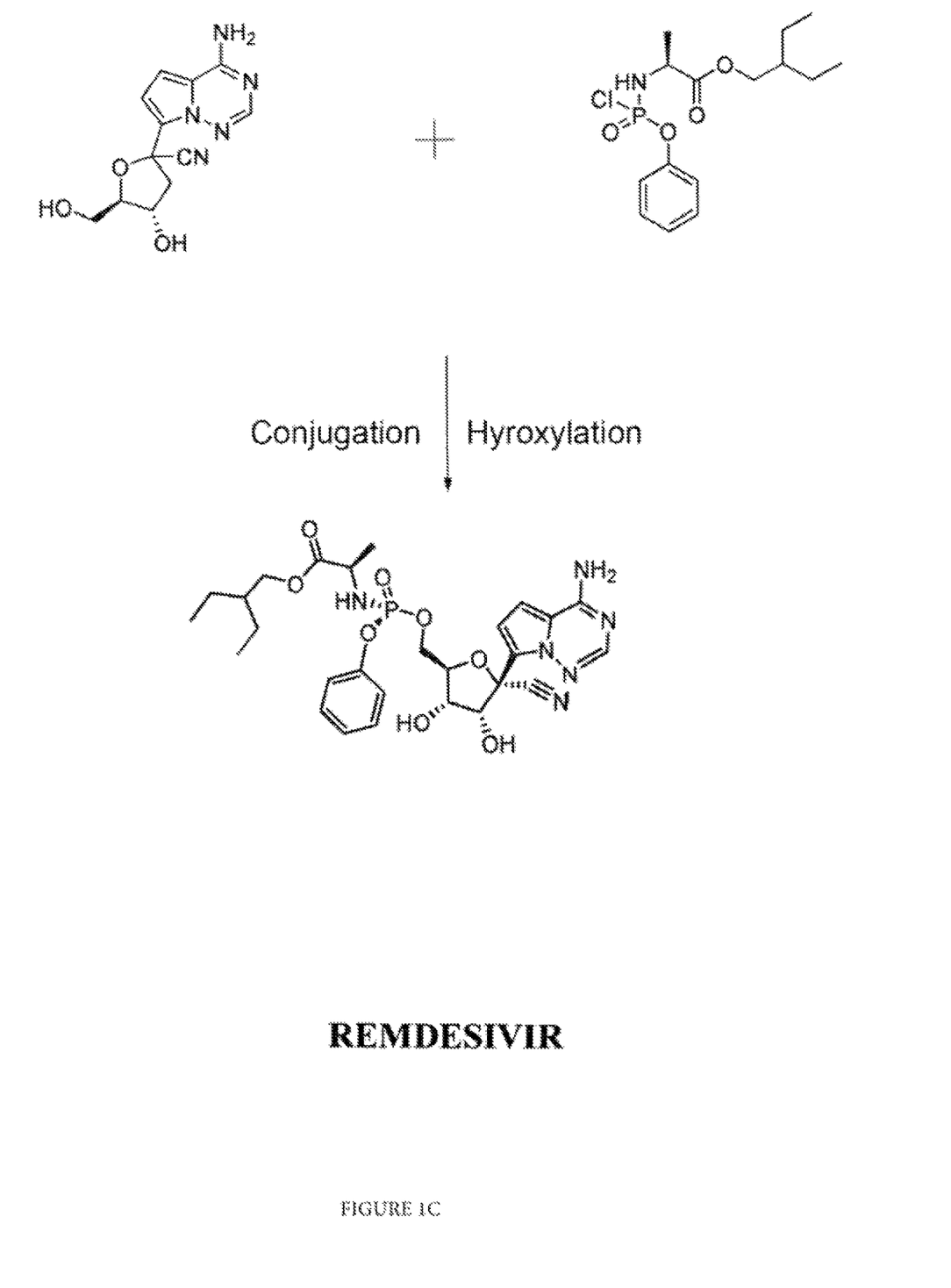

The present invention includes a new form of Remdesivir having improved water solubility and a new synthetic method for preparing the same. The present invention also includes pharmaceutical compositions containing this new form of Remdesivir that is more soluble in water and/or more stable at room temperature in combination with one or more known pharmaceutically-acceptable excipients. One such pharmaceutical compositions is a dry powder containing this new form of Remdesivir that is substantially free of water following a dehydration or lyophilization process.

The present invention also includes methods of preventing and/or treating viral infections, particularly Coronavirus infections, by administering to a patient in need thereof a therapeutically effective amount of the new form of Remdesivir having improved water solubility.

II. Definitions

As used herein, the following definitions shall apply unless otherwise expressly noted in the text:

The term "pH adjusting agent" refers to one or more buffers, acids, and bases or combinations thereof.

An "acid" is a compound that is capable of donating a proton ($H^+$) under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, camphorsulfonic acid, among others.

A "base" is a compound capable of accepting a proton under the Bronsted-Lowry definition, or is an electron-pair donor under the Lewis definition. Bases useful in the present invention that are Bronsted-Lowry bases include hydroxides such as lithium hydroxide, sodium hydroxide, potassium hydroxide, rubidium hydroxide, cesium hydroxide, magnesium hydroxide, strontium hydroxide, barium hydroxide, and others. Lewis bases include, but are not limited to, amines such as ammonia, trimethylamine, triethylamine, diisopropylethylamine (DIPEA or Hunig's Base), 1,8-diazabicycloundec-7-ene (DBU), 2,6-di-tert-butylpyridine, quinuclidine, and lithium di-isopropylamine (LDA), and nucleophilic bases such as butyl-lithium. Other bases are known to one of skill in the art.

A "buffer" is a mixture of a weak acid and its conjugate base, or a weak base and its conjugate acid, whose pH changes very little when a small amount of strong acid or base is added to it. Examples of suitable buffers commonly used in parenteral products include, but are not limited to, phosphoric acid/phosphate, acetic acid/acetate, citric acid/citrate, tartaric acid/tartrate, aspartic acid/aspartate, glutamic acid/glutamate, succinic acid/succinate, and lactic acid/lactate.

The terms "dehydrate" and "dehydration" refer to the process of removing water from a sample via evaporation, sublimation, or a combination thereof. "Evaporation" refers to the transition of a substance from a liquid state to a gaseous state, and "sublimation" refers to the transition from a solid state directly to a gaseous state. Dehydration can occur at a variety of temperatures and pressures. When dehydration occurs below the freezing point of the sample, this is referred to as freeze-drying or lyophilizing, the process of removing water from a sample at low temperature and pressure.

The terms "treatment" and "treating" refer to the administration of a composition according to the present invention to a mammalian subject (e.g. a human) having or susceptible to a condition or disease disclosed herein for the purpose of: (a) preventing or protecting against the disease or condition, that is, causing the clinical symptoms not to develop; (b) inhibiting the disease or condition, that is, arresting or suppressing the development of clinical symptoms; and/or (c) relieving the disease or condition that is causing the regression of clinical symptoms.

The terms "patient" and "subject" refer to mammals, including, but not limited to, primates (e.g., humans), cows, sheep, goats, horses, dogs, cats, rabbits, rats, mice and the like. In certain embodiments, the subject is a human.

The term "therapeutically effective amount" refers to the amount of Remdesivir, or a pharmaceutically acceptable salt thereof, present in a composition described herein that is needed to provide a desired level of drug in the secretions and tissues of the airways and lungs, or alternatively, in the bloodstream of a subject to be treated so as to give an anticipated physiological response or desired biological effect when such a composition is administered by the chosen route of administration. The precise amount involved will depend upon numerous factors, including the specific activity of the composition, the delivery device employed, the physical characteristics of the composition, and its intended use, as well as patient-dependent factors, such as severity of the disease state, co-morbidities, etc., and can readily be determined by one skilled in the art based upon the information provided herein.

The terms "safe water for injection" and "water safe for infection" and "sterile water for injection" refer to water suitable for combining with one or more drugs requiring dilution or dissolution prior to administration to a subject in need thereof. The water for injection is sterile and stored in a glass vial of Type I or II borosilicate glass, or other suitable container. The water for injection does not include any other components, such as stabilizers, antimicrobial agents, buffer, etc.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

III. Formulations

All compositions described here contain a predetermined amount of Remdesivir prepared according to the methods of the present injection, or a pharmaceutically acceptable salt thereof, and, optionally, one or more pH adjusting agents or other pharmaceutically acceptable excipients.

A. Solution Composition

In some embodiments of the present invention, the composition also includes water to form a solution composition. The water can be any suitable water, such as distilled water or water safe for injection. In some embodiments of the present invention, the water can be water safe for injection.

Any suitable number of pH adjusting agents can be used in the composition of the present invention. For example, the composition can includes, 1, 2, 3, 4 or more pH adjusting agents, such as NaOH and HCl. In some embodiments, the composition includes at least one pH adjusting agent. In some embodiments, the composition includes at least 2 pH adjusting agents. When more than 1 pH adjusting agent is used, the pH adjusting agents can be acids, bases, or a mixture thereof. In some embodiments, a first pH adjusting agent includes an acid, such as HCl, and a second pH adjusting agent includes a base, such as NaOH.

The solution composition of the present invention preferably has a pH of less than 7, more preferably less than about 6, 5, or 4. The pH of the solution composition can be in the range of from 1 to 6, 2 to 5, or 3 to 4. For example, the pH of the solution composition can be about 3.1, 3.2, 3.3, 3.4, 3.5, 3.6, 3.7, 3.8, or about 3.9. In some embodiments, the solution composition has a pH of from 3 to 4. In some embodiments, the solution composition has a pH of about 3.5.

According to certain embodiments of the present invention, the solution composition contains a therapeutically effective amount of Remdesivir. Preferably, the therapeutically effective amount is sufficient for once-a-day administration to a patient in need thereof. Alternatively, the therapeutically effective amount in solution composition is a fraction of the daily dose, e.g., ½, ¼, etc., required for the patient to which it is to be administered.

In some embodiments of the present invention, the solution composition contains 25 mg to 200 mg of Remdesivir or an equivalent amount of a pharmaceutically acceptable salt thereof. In some preferred embodiments, the solution composition contains 25 mg to 100 mg of Remdesivir or an equivalent amount of a pharmaceutically acceptable salt thereof. In other preferred embodiments, the solution composition contains 25 mg. 50mg, or 100 mg of Remdesivir or an equivalent amount of a pharmaceutically acceptable salt thereof. In certain preferred embodiments, the solution contains 100 mg of Remdesivir or an equivalent amount of a pharmaceutically acceptable salt thereof.

In some embodiments of the present invention, Remdesivir is present at about 1.0 to 10.0 mg/mL. In some embodiments, Remdesivir is present at about 4.0 to 8.0 mg/mL. In some embodiments, Remdesivir is present at about 5.0 to 7.0 mg/mL. In some embodiments, Remdesivir is present at about 5.0 mg/mL.

B. Lyophilized Composition

The compositions of the present invention also includes a lyophilized or dehydrated composition of Remdesivir prepared by the inventive method, or a pharmaceutically acceptable salt thereof. The lyophilized composition can be in any suitable solid form, such as a powder.

Remdesivir prepared according to the methods of the present invention can be present in a lyophilized composition in an amount from 1% to 10% (w/w), or from I to 5%, or from 2 to 4%, or from 3 to 4%, or from 3 to 3.5% (w/w). In some embodiments, the lyophilized composition includes Remdesivir prepared by the inventive method in an amount from 1% to 10% (w/w). In some embodiments, the lyophilized composition include Remdesivir prepared by the inventive method in an amount from 1% to 5% (w/w). In some embodiments, the lyophilized composition includes Remdesivir prepared by the inventive method in an amount from 2% to 4% (w/w). In some embodiments, the lyophilized composition includes Remdesivir prepared by the inventive method in an amount from 3% to 3.5% (w/w).

Remdesivir prepared by the inventive method can be present in the lyophilized composition in an amount of about 1% (w/w), or 1.5, 2, 2.1, 2.2, 2.3, 2.4, 2.5, 2.6, 2.7, 2.8, 3.9, 3, 3.1, 3.2, 3.3, 3.4, 3.5, 3.6, 3.7, 3.8, 3.9, 4, 43, 5, 6, 7, 8, 9, or about 10% (w/w). In some embodiments, the lyophilized composition includes Remdesivir prepared by the inventive method at about 3.2% (w/w).

The lyophilized compositions of the present invention are surprisingly stable, showing relatively little impurity formation when tested at raised temperatures and relative humidity. For example, the purity of the lyophilized composition can be at least 95%, or 96, 97, 98, 99, 99.1, 99.2, 99.3, 99.4, 99.5, 99,6, 99.7, 99.8, or at least 99.9%. Thus, the lyophilized compositions can have an impurity in the amount of less than 5%, or 4, 3, 2, 1, 0.9, 0.8, 0.7, 0.6, 0.5, 0.4, 0.3, 0.2, or less than 0.1%. In some embodiments, the lyophilized composition has less than about 1% of any impurity, preferably less than about 0.5%, as determined by HPLC after one or more of the following scenarios: (i) storage for 18 months at a temperature of about 25° C. (±1° C.) and a relative humidity of about 60% (±1%); (ii) storage for 18 months at a temperature of about 30° C. (±1° C.) and a relative humidity of about 75% (±1%); or (iii) storage for 6 months at a temperature of about 40° C.±1° C.) and a relative humidity of about 75% (±1%).

The lyophilized composition can include various forms of Remdesivir prepared according to the methods of the present invention. For example, Remdesivir prepared according to the methods of the present invention can be amorphous or crystalline, or a mixture thereof. In some embodiments, the lyophilized composition includes amorphous Remdesivir prepared according to the methods of the present invention.

The lyophilized compositions can be contained in any suitable container, such as a sealed vial. In some embodiments, the present invention provides a sealed vial containing the lyophilized composition. In some embodiments, the present invention provides a sealed vial containing a lyophilized composition consisting essentially of Remdesivir prepared according to the methods of the present invention.

C. Injectable Composition

The compositions of the present invention also includes an injectable composition for administration to subjects and patients in need of treatment. The injectable composition includes the lyophilized compositions described above, and water. In some embodiments, the present invention provides an injectable composition that includes Remdesivir prepared according to the inventive methods, or a pharmaceutically acceptable salt thereof, in an amount from 0.1% to 10% w/v; and water.

The water of the injectable compositions can be any suitable type of water. For example, the water of the injectable composition can be water safe for injection or sterile water for injection.

The injectable compositions include any suitable amount of Remdesivir prepared according to the methods of the present invention from 0.1% to 10% w/v. For example, Remdesivir prepared according to the methods of the present invention can be present in the injectable composition in an amount from 0.1% to 5% w/v, 0.1 to 4, 0.1 to 3, 0.1 to 2, 0.1 to 1, 0.2 to 0.8, 0.3 to 0.7, or 0.4% to 0.6% w/v. Remdesivir prepared according to the methods of the present invention can be present in the injectable composition in an amount of about 0.1% w/v, or 0.2, 0.3, 0.4, 0.5, 0.6, 0.7, 0.8, 0.9, or about 1% w/v. In some embodiments, Remdesivir prepared according to the methods of the present invention is present in the injectable composition in an amount of 0.1% to 10% w/v. In some embodiments, Remdesivir prepared according to the methods of the present invention is present in the injectable composition in an amount of 0.1% to 1% w/v. In some embodiments, Remdesivir prepared according to the methods of the present invention is present in the injectable composition in an amount of about 0.5% w/v.

The injectable composition include any suitable amount of Remdesivir prepared according to the methods of the present invention from 0.1 to 100 mg/mL. For example, Remdesivir prepared according to the methods of the present invention can be present in the injectable composition in an amount from 0.1 to 100 mg/mL, or 0.1 to 50, 0.5 to 10, 1 to 10, 2 to 8, 3 to 7, 4 to 6, or 4.5 to 5.5 mg/mL. Remdesivir prepared according to the inventive methods can be present in the injectable composition in an amount of about 0.1 mg/mL, or 0.5, 1, 2, 2.5, 3, 3.5, 4, 4.5, 4.6, 4.7, 4.8, 4.9, 5, 5.1, 5.2, 5.3, 5.4, 5.5, 6, 6.5, 7, 7.5, 8, 8.5, 9, 9.5, 10, 15, 20 or 25 mg/mL. In some embodiments, Remdesivir prepared according to the methods of the present invention is present in the injectable composition in an amount of 1 to 10 mg/mL. In some embodiments, Remdesivir prepared according to the methods of the present invention is present in the injectable composition in an amount of 4 to 6 mg/mL. In some embodiments, Remdesivir prepared according to the inventive methods is present in the injectable composition in an amount of about 5 mg/mL.

The injectable composition can be contained in any suitable container, such as a sealed vial. In some embodiments, the present invention provides a sealed vial containing the injectable composition. In some embodiments, the present invention provides a sealed vial containing the injectable composition consisting essentially of Remdesivir prepared according to the methods of the present invention in an amount of about 0.5% w/v, and water safe for injection.

IV. Methods of Treating

In some embodiments, the present invention provides a method of treating a viral infection comprising administering a pharmaceutical composition comprising Remdesivir prepared according to the methods of the present invention, or a pharmaceutically acceptable salt thereof, and, optionally, pH adjusting agents.

In some embodiments, the present invention provides a method of treating a viral infection comprising administering a pharmaceutical composition comprising a therapeutically effective amount of Remdesivir prepared according to the methods of the present invention, or a pharmaceutically acceptable salt thereof, and, optionally, pH adjusting agents.

In some embodiments, the present invention provides a method of treating a viral infection comprising parenterally administering a pharmaceutical composition comprising Remdesivir prepared according to the methods of the present invention, or a pharmaceutically acceptable salt thereof, and, optionally, pH adjusting agents.

In some embodiments, the present invention provides a method of treating a viral infection comprising (a) reconstituting with safe water for injection a lyophilized pharmaceutical composition comprising Remdesivir prepared according to the methods of the present invention, or a pharmaceutically acceptable salt thereof, and (b) administering the reconstituted pharmaceutical composition to a patient in need thereof.

In some embodiments, the present invention provides a method of treating a viral infection comprising (a) reconstituting with safe water for injection a lyophilized pharmaceutical composition comprising Remdesivir prepared according to the methods of the present invention, or a pharmaceutically acceptable salt thereof, and (b) parenterally administering the reconstituted pharmaceutical composition.

In some embodiments, the parenteral administration is selected from the group consisting of intramuscular (IM), subcutaneous (SC) and intravenous (IV) administrations.

In some embodiments, the present invention provides a method of treating a virus comprising parenterally administering a pharmaceutical composition comprising Remdesivir prepared according to the methods of the present invention, or a pharmaceutically acceptable salt thereof, and, optionally, pH adjusting agents. In some embodiments, the present invention provides a method of treating a virus comprising parenterally administering a pharmaceutical composition comprising Remdesivir prepared according to the methods of the present invention, or a pharmaceutically acceptable salt thereof, wherein the virus is an Arenaviridae virus, a Coronaviridae virus, a Filoviridae virus, a Flaviviridae virus or a Paramyxoviridae virus. In some embodiments, the present invention provides a method of treating a virus comprising parenterally administering a pharmaceutical composition comprising Remdesivir prepared according to the methods of the present invention, or a pharmaceutically acceptable salt thereof, wherein the virus is Lassa, Junin, Severe Acute Respiratory Syndrome (SARS), SARS-CoV-2, Middle Eastern Respiratory Syndrome (MERS), ebolavirus, Marburg virus, Zika, or Respiratory Syncytial virus. In some embodiments, the present invention provides a method of treating a virus comprising parenterally administering a pharmaceutical composition comprising Remdesivir prepared according to the methods of the present invention, or a pharmaceutically acceptable salt thereof, wherein the virus is Lassa, Junin, Severe Acute Respiratory Syndrome (SARS), SARS-CoV-2, Middle Eastern Respiratory Syndrome (MERS), other human coronaviruses (229E, NL63, OC43, HKU1, or WIV1), zoonotic coronaviruses (PEDV or HKU CoV isolates such as HKU3, HKU5, or HKU9), ebolavirus (variants Zaire, Bundibugio, Sudan, Tai forest, or Reston), Marburg virus, Nipah, Hendra, Measles, Mumbs, Dengue, Yellow Fever, West Nile Virus, Zika, Parainfluenza, Metapneumovirus or Respiratory Syncytial virus.

In some embodiments, the present invention provides a method of treating a virus comprising parenterally administering a pharmaceutical composition comprising Remdesivir prepared according to the methods of the present invention, or a pharmaceutically acceptable salt thereof, and, optionally, one or more pH adjusting agents, wherein the virus is SARS-CoV-2.

V. Methods of Preparing

The lyophilized compositions of the present invention can be prepared by means generally known to one of skill in the art for removing water from a substance. For example, the compositions can be dehydrated by heating the sample to a suitable temperature for a suitable period of time. The compositions can also be dehydrated under a reduced pressure atmosphere at any suitable temperature. The reduced pressure atmosphere can be any pressure less than atmospheric pressure. The reduced pressure atmosphere can be heated to a temperature above room temperature, be maintained at about room temperature, or cooled to a temperature below room temperature. For example, the compositions can be cooled to a temperature of less than room temperature while under a reduced pressure atmosphere. Suitable temperatures include, but are not limited to, less than room temperature, or less than 20° C., 15, 10, 5, 0, −5, −10, −15, −20, −25, −30, −40, or less than −50° C. When a reduced pressure atmosphere is used, the reduced pressure atmosphere can be less than atmospheric pressure, or less than 100 torr (mm Hg), 50, 25, 10, 5, 4.58 (the triple point for water), 4, 3, 2, 1, 0.5, 0.1, 0.05, or less than 0.01 torr. The compositions can be cooled to a temperature of less than 0.01° C. while under a reduced pressure atmosphere of less than 4.58 torr (611 Pascal or 0.006 atmospheres).

The compositions of the present invention can be prepared according to the methods described in the examples below and variations thereof understood by one of skill in the art. For example, the lyophilized composition of the present invention can be prepared by adding Remdesivir prepared according to the methods of the present invention to water, adjusting the pH of the mixture as needed to form an aqueous solution of Remdesivir prepared according to the methods of the present invention, and adding water to the solution as needed to form a composition wherein the Remdesivir is present at a predetermined concentration, such as about 6.7 mg/mL, and then lyophilizing the mixture.

Remdesivir prepared according to the methods of the present invention can be used in any suitable amount to achieve the desired concentration in mixture prior to lyophilization. For example, Remdesivir prepared according to the inventive methods can be present in an amount of 1 mg to 1000 mg, or 5 to 500, or 50 to 250, or 60 to 240, or 70 to 230, or 80 to 220, or 90 to 210, or 100 to 200, or 90 to 110, or 145 to 165, or 90 mg to 175 mg. Remdesivir prepared according to the methods of the present invention can also be present in an amount of about 10 mg, or about 20, 30, 40, 50, 60, 70, 80, 90, 100, 110, 120, 130, 140, 150, 160, 170, 180, 190, 200, 210, 220, 230, 240, or about 250 mg.

Remdesivir prepared according to the methods of the present invention can be of any suitable form. For example, Remdesivir prepared according to the methods of the present invention can be amorphous or crystalline. In some embodiments, Remdesivir prepared according to the methods of the present invention is amorphous, whereas in others it is crystalline.

Remdesivir prepared according to the methods of the present invention can have any suitable purity, such as at least 90%, or at least 91, 92, 93, 94, 95, 96, 97, 98, 99, or at least 99.1, 992, 99.3, 99.4, 99.5, 99.6, 99.7, 99.8 or at least 99.9%. In some embodiments, Remdesivir prepared according to the methods of the present invention has a purity of at least 99.1%. In some embodiments, Remdesivir prepared according to the methods of the present invention, and in others at least 99.7%. The impurities present in Remdesivir prepared according to the methods of the present invention can include unreacted starting material, undesirable side-products, and other materials.

According to preferred embodiments of the present invention, Remdesivir is prepared by the following multi-step synthesis:

(a) reacting (3R,4R,5R)-3,4-bis(benzyloxy)-5-((benzyloxy)methyl)dihydrofuran-2(3H)-one with iodopyrazole in presence of boron trichloride in an organic solvent at room temperature to form (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol;

(b) cyanating the (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol formed in (a) to produce (3R,4R,5R)-2-(4-aminopyrrolo[2,1-f][1,2,4]triazin-7-yl)-3,4-bis(benzyloxy)-5-((benzyloxy) methyl)tetrahydrofuran-2-carbonitrile;

(c) hydrolyzing the (3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile produced in (b) in presence of boron trichloride to give (3R,4S,5R)-2-(4-aminopyrrolo[2,1-f][1,2,4]triazin-7-yl)-3,4-dihydroxy-5-(hydroxymethyl)tetrahydrofuran-2-carbonitrile; and (d) condensing the (3R,4S,5R)-2-(4-aminopyrrolo[2,1-f][1,2,4]triazin-7-yl)-3,4-dihydroxy-5-(hydroxymethyl)

tetrahydrofuran-2-carbonitrile formed in (c) with 2-ethylbutyl (chloro(phenoxy)phosphoryl)-L-alaninate to produce Remdesivir.

According to other preferred embodiments of the present invention, reaction (d) above is replaced by:
(d1) reacting (3R,4S,5R)-2-(4-aminopyrrolo[2,1-f][1,2,4]triazin-7-yl)-3,4-dihydroxy-5-(hydroxymethyl)tetrahydrofuran-2-carbonitrile formed in (c) with 2,2 dimethoxy propane in the presence of PTSA and isopropylacetate to form (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile; and
(d2) reacting the (3aR,4R,6R,6aR)-4-(4-aminopyrrolo[2,1-f][1,2,4]triazin-7-yl)-6-(hydroxymethyl)-2,2-dimethyltetrahydrofuro[5 3,4-d][1,3]dioxole-4-carbonitrile formed in (d1) with t-BuMgCl in presence of 2-ethylbutyl (chloro(phenoxy)phosphoryl)-L-alaninate to produce Remdesivir.

EXAMPLES

Example 1

Preparation of 2-ethylbutyl(chloro(phenoxy)phosphoryl)-L-alaninate 2-ethylbutyl (chloro(phenoxy)phosphoryl)-L-alaninate was prepared by the process reported in US'360. Accordingly, Phenyl dichlorophosphate was 20 reacted with 2-ethylbutyl alanine ester in presence of trimethylamine and methylene dichloride solvent to obtain 2-ethylbutyl (chloro(phenoxy)phosphoryl)-L-alaninate.

Example 2

Preparation of (3R,4R,5R)-3,4-bis(benzyloxy)-5-((benzyloxy)methyl)dihydro furan-2(3H)-one (3R,4R,5R)-3,4-bis(benzyloxy)-5-((benzyloxy)methyl) dihydrofuran-2(3H)-one was prepared by the process reported in US'360. Accordingly, (3R,4R,5R)-3,4-bis (benzyloxy)-5-((benzyloxy)methyl) tetrahydrofuran 2-ol was reacted with acetic anhydride in DMSO to obtain (3R,4R,5R)-3,4-bis(benzyloxy)-5-((benzyloxy)methyl)dihydrofuran-2(3H)-one.

Example 3

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile To the compound of example 2 (50 gm) was charged MDC and the reaction mass was cooled to −75±5 oC followed by addition of trifluoromethane sulfonic acid (15 ml) at same temperature, stirred to get the thick mass. To the mass was added TMSOTf (12.5 ml), stirred at same temperature, added TMSCN (50 ml), stirred reaction mass for 2 hrs. After completion of reaction, was added TEA (40 ml) at −75±5° C., raised the temperature to 30±5° C., charged NaHCO₃ (50 gm), water (300 ml) and allowed to settle the mass at room temperature. The reaction mass was extracted with MDC, washed the organic layer with 10% NaCl solution, distilled the organic layer under vacuum below 45° C., cooled, dried to obtain the product. Yield: 60-65 gm: HPLC purity: NLT 98.0%

Example 4

Preparation of (3R,4S,5R)-2-(4-aminopyrrolo[2,1-f][1,2,4]triazin-7-yl)-3,4-dihydroxy-5-(hydroxymethyl)tetrahydrofuran-2-carbonitrile To the intermediate of example −4 (50 gm) was charged DCM (500 ml) at 30±5° C., stirred, cooled to −75±5° C. then slowly added BCl₃(1M) solution in DCM (500 ml) over a period of 1 hr, stirred for 2 hrs at the same temperature. After completion of the reaction (by TLC), the reaction mass was quenched with methanol (100 ml), slowly added TEA (150 ml) dissolved in methanol (200 ml) to the reaction mass at −75±5° C. Gradually raised the temperature to 30±5° C. Distilled out the solvent under vacuum at 30° C., decanted the residue with hexane mass (3×100 ml), charged methanol (400 ml) at 30±5° C., gradually raised the temperature to 45±5° C., slowly added water (500 ml) at the same temperature, stirred the reaction mass, distilled out the solvent under vacuum at 45±5° C., filtered, washed and dried. Dry weight: 20.1 gm Example 5

Preparation of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile To the compound (3R,4S,5R)-2-(4-aminopyrrolo[2,1-f][1,2,4]triazin-7-yl)-3,4-dihydroxy-5-(hydroxymethyl)tetrahydrofuran-2-carbonitrile was added 2,2 dimethoxy propane (104 ml) in acetone (250 ml) at 30±5° C., stirred the reaction mass for 15 mins and charged PTSA at the same temperature, stirred the reaction mass, slowly added isopropyl acetate (100 ml) at the same temperature and stirred the reaction mass for an hr. After completion of the reaction (by TLC), filtered the solid and washed with heptane and isopropyl acetate (250 ml) in 2:1 ratio to obtain the solid, which is vacuum dried. Charged ethyl acetate (500 ml) and charged 5% potassium carbonate solution (500 ml) and back extracted the aqueous mass into ethyl acetate, combined the organic layers, washed with water and dried over sodium sulfate (50 gm). Distilled solvent under vacuum below 45° C., added heptane (500 ml), stirred and filtered the product, washed the product with heptane (50 ml); such dried followed by vacuum dried below 30° C. and further dried at 40° C., to obtain the product. Yield: 45-50 gm; HPLC purity: NLT 98.0%

Example 6

Preparation of (2S)-2-ethylbutyl 2-(((((2R3S4R,5R)-5-(4-aminopyrrolo [2,1-f]1,2,4 triazin-7-yl)-5-cyano-3,4-dihydroxytetrahydrofuran-2-yl)methoxy)(phenoxy)phosphoryl)amino) propanoate To the compound (3R,4S,5R)-2-(4-aminopyrrolo[2,1-f][1,2,4]triazin-7-yl)-3,4-dihydroxy-5-(hydroxymethyl)tetrahydrofuran-2-carbonitrile (25 gm) of example 6 was added THF (250 ml) at 30±5° C. to obtain the homogenous mass. Gradually cooled to −40±3° C. and slowly added t-BuMgCl (87 ml) at −40±3° C. over a period of 30-45 mins, stirred, and slowly added 2-ethylbutyl (chloro(phenoxy)phosphoryl)-L-alaninate (56 ml) dissolved in THF (150 ml) at −40±3° C. Gradually raised the temperature to 10±5° C., stirred. After testing with HPLC, cooled the reaction mass at −40±3° C., quenched the reaction mass with methanol (250 ml), stirred, raised the temperature to 25±5° C., charged DCM (750 ml), and 10% ammonium chloride (500 ml), stirred washed the organic layer with 5% K$_2$CO$_3$, allowed to settle, separated the organic layer and dried over sodium sulfate (80 gm) and distilled the solvent under vacuum at below 45° C. to obtain the solid mass. Cooled the mass to 10-15° C., added water (2000 ml) and MDC (1000 ml), stirred and allowed to settle. Separated the lower MDC layer and to the aqueous layer was added MDC (500 ml) stirred and settled and separated the lower MDC layer. To the total organic layer was added brine solution, stirred, separated lower MDC layer, cooled to 0-5° C., adjusted the pH to 6.5 with NaHCO$_3$, stirred, settled, separated the MDC and aq. layer and to the combined organic layer was added brine. Distilled the MDC layer to obtain (2S)-2-ethylbutyl 2-(((((2R,3S,4R,5R)-5-(4-aminopyrrolo[2,1-f]1,2,4 triazin-7-yl)-5-cyano-3,4-dihydroxytetrahydrofuran-2-yl)methoxy)(phenoxy)phosphoryl)amino)propanoate.

Example 7

(2S)-2-ethylbutyl 2-(((((2R,3S,4R,5R)-5(4-aminopyrrolo[2, triazin-7-yl)-5-cyano-3,4-dihydroxy oxalan-2-yl]methoxy)(phenoxy)phosphoryl)amino)propanoate To the compound (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (25 gm) of example 5 was added THF (250 ml) at 30±5° C. to obtain the homogenous mass. Gradually cooled to −40±3° C. and slowly added t-BuMgCl (87 ml) at −40±3° C. over a period of 30-45 10 mins, stirred, and slowly added 2-ethylbutyl (chloro(phenoxy)phosphoryl)-L-alaninate (56 ml) dissolved in THF(150 ml) at −40±3 oC. Gradually raised the temperature to 10±5° C., stirred. After testing with HPLC, cooled the reaction mass at −40±3° C., quenched the reaction mass with methanol (250 ml), stirred, raised the temperature to 25±5° C., charged DCM (750 ml), and 10% ammonium chloride (500 ml), stirred washed the organic layer with 5% K$_2$CO$_3$, allowed to settle, separated the organic layer and dried over sodium sulfate (80 gm) and distilled the solvent under vacuum at below 45° C. to obtain the solid mass. Cooled the mass to 10-15° C., added water (2000 ml) and MDC (1000 ml), stirred and allowed to settle. Separated the lower MDC layer and to the aqueous layer was added MDC (500 ml) stirred and settled and separated the lower MDC layer. To the total organic layer was added brine solution, stirred, separated lower MDC layer, cooled to 0-5° C., adjusted the pH to 6.5 with NaHCO$_3$, stirred, settled, separated the MDC and aq. layer and to the combined organic layer was added brine. Distilled the MDC layer to obtain crude (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy) (phenoxy)phosphoryl)amino) propanoate. Yield 96 to 100 gm Example 8

Preparation of Remdesivir

To the residue of example 7 (96 gm) was added THF (1000 ml) at 30±5° C., stirred, cooled to 3±3U/N2C. Added acetic acid (192 ml) at 3±5° C., followed by addition of conc. HCl (96 ml) at same temperature. Raised the temperature to30±5° C., maintained for 1-2 hr, sample sent for HPLC. This was followed by adding water (480 ml), cooled the mass to 3±5° C., adjusted the pH with K$_2$CO$_3$(10% solution) and extracted into ethyl acetate (2000 ml). Washed the combined extracts with sat. NaCl (350 gm in 1000 ml) and the organic layer dried over sodium sulfate. Distilled the solvent under vacuum at below 45° C., degassed the residue under vacuum. The residue was then stripped with isopropyl acetate (50 ml), cooled the reaction at 30±5° C., stirred, filtered, rinsed with isopropyl acetate, distilled the filtrate under vacuum to obtain the residue. Charged ethanol to the residue after HPLC analysis at 30±5° C., raised the temperature to 50±5° C. Maintained at same temperature, stirred, cooled, filtered and dried to obtain Remedesivir (42.8 gm). HPLC purity: NLT 99.0%.

It is to be understood that the invention as described herein is merely a preferred embodiment. Various changes may be made in the amounts of components and reagents; equivalent components and reagents may be substituted for those illustrated and described; and certain features may be used independently from others without departing from the spirit and scope of the invention as defined in the following claims.

What is claimed is:

1. A method for the synthesis of Remdesivir, which comprises: (a) reacting (3R,4R,5R)-3,4-bis(benzyloxy)-5-((benzyloxy)methyl)dihydrofuran-2(3H)-one with a halo-pyrazole in presence of boron trichloride in an organic solvent at room temperature; (b) cyanating (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol; (c) hydrolysing (3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile in presence of boron trichloride; and (d) condensing (3R,4S,5R)-2-(4-aminopyrrolo[2,1-f][1,2,4]triazin-7-yl)-3,4-dihydroxy-5-(hydroxymethyl)tetrahydrofuran-2-carbonitrile with 2-ethylbutyl (chloro(phenoxy)phosphoryl)-L-alaninate.

2. The method according to claim I, wherein (d) is replaced by: (d1) reacting (3R,4S,5R)-2-(4-aminopyrrolo[2,1-f][1,2,4]triazin-7-yl)-3,4-dihydroxy-5-(hydroxymethyl)tetrahydrofuran-2-carbonitrile with 2,2 dimethoxy propane in presence of PTSA and isopropylacetate; and (d2) reacting (3aR,4R,6R,6aR)-4-(4-aminopyrrolo[2,1-f][1,2,4]triazin-7-yl)-6-(hydroxymethyl)-2,2-dimethyltetrahydrofuro[5 3,4-d][1,3]dioxole-4-carbonitrile with t-BuMgCl in presence of 2-ethylbutyl (chloro(phenoxy)phosphoryl)-L-alaninate.

3. The method of claim 1, wherein the halo-pyrazole in (a) is iodopyrazole or bromopyrazole.

4. The method of claim 2, wherein the halo-pyrazole in (a) is iodopyrzole or bromopyrazole.

* * * * *